US006350576B1

(12) United States Patent
Wigler et al.

(10) Patent No.: US 6,350,576 B1
(45) Date of Patent: *Feb. 26, 2002

(54) CANCER DETECTION PROBES

(75) Inventors: Michael Wigler, Lloyd, NY (US); Nikolai Lisitsyn, Philadelphia, PA (US)

(73) Assignee: Cold Spring Harbor Laboratory, Cold Spring Harbor, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/576,202

(22) Filed: Dec. 21, 1995

Related U.S. Application Data

(63) Continuation-in-part of application No. 08/360,096, filed on Dec. 20, 1994, now Pat. No. 5,569,753.

(51) Int. Cl.$^7$ ............ C12Q 1/68; C07H 21/02; C07H 21/04; C12N 15/00

(52) U.S. Cl. ............ 435/6; 536/23.1; 536/24.3; 935/76; 935/77; 935/78

(58) Field of Search ............ 435/6; 536/23.1, 536/24.3; 935/76, 77, 78

(56) References Cited

U.S. PATENT DOCUMENTS

| 4,683,202 A | * | 7/1987 | Mullis ............ 435/6 |
| 5,472,842 A | * | 12/1995 | Stokke et al. ............ 435/6 |
| 5,569,753 A | * | 10/1996 | Wigler et al. ............ 536/24.3 |
| 5,616,463 A | * | 4/1997 | Fornace et al. ............ 435/6 |
| 5,856,097 A | * | 1/1999 | Pinkel et al. ............ 435/6 |

FOREIGN PATENT DOCUMENTS

| WO | 94/11383 | 5/1994 |
| WO | 96/19589 | 6/1996 |

OTHER PUBLICATIONS

T'Ang et al., Structural Rearrangement of the Retinoblastoma Gene in Human Breast Carcinoma. Science 242 : 263–266 (1988).*
Wahl et al., Cosmid Vectors for Rapid Genomic Walking, Restriction Mapping, and Gene Transfer. PNAS 84 : 2160–2164 (1987).*
Triglia et al., A Procedure for in vitro Amplification of DNA Segments that Lie Outside the Boundries of Known Sequences. Nucleic Acids Research 16(16) : 8186 (1988).*
Newman et al., PECAM–1 (CD31) Cloning and Relation to Adhesion Molecules of the Immunoglobulin Gene Superfamily. Science 247 : 1219–1222 (1990).*

Lisitsyn, N.A., "Representational difference analysis: finding the difference between genomes", TIG, vol. 11(8), pp. 303–307, Aug. 1995.
Lisitsyn, N.A. et al., "Detection of Genetic Loss in Tumors by Representational Difference Analysis", Cold Spring Harbor Symposia on Quantitative Biology, vol. LIX, pp. 585–587, 1994.
Lisitsyn, N., et al., "Representational Difference Analysis in Detection of Genetic Lesions in Cancer", Methods in Enzymology, vol. 254, pp. 291–304, 1995.
Kirschbaum, N.E., et al. "Organization of the Gene for Human Platelet/Endothelial Cell Adhesion Molecule–1 Shows Alternatively Spliced Isoforms and a Functionally Complex Cytoplasmic Domain", Blood, 84(12), pp. 4028–4037, Dec. 15, 1994.
Solomon et al., "Chromosome Aberrations and Cancer", Science (1991), 254:1153.
Lasko et al., "Loss of Constitutional Heterozygosity in Human Cancer", Annu. Rev. Genet. (1991), 25:281–314.
Lisitsyn et al., "Cloning the Differences Between Two Complex Genomes", Science (1993), 259:946–951.
Lisitsyn et al., "Direct Isolation of Polymorphic Markers Linked to a Trait by Genetically Directed Representational Difference Analysis", Nature Genetics (1994), 6:57–63.
Presti Jr., et al., "Histopathological, Cytogenic, and Molecular Characterization of Renal Cortical Tumors", Cancer Research (1991), 51:1544–1552.
Schwab et al., "Amplification of Cellular Oncogenes: A Predictor of Clinical Outcome in Human Cancer", Genes, Chromosomes & Cancer (1990), 1:181–193.
Lisitsyn et al., "Comparative Genomic Analysis of Tumors: Detection of DNA Losses and Amplification", PNAS USA (1995), 92:151–155.
Chang et al., "Identification of Herpesvirus–Like DNA Sequences In AIDS–Associated Kaposi's Sarcoma", Science (1994), 266:1865–1869.
Cohen, "Is a New Virus The Cause of KS?" Science (1994), 266:1803–1804.
Pool, Can Sound Drive Fusion in a Bubble?, Science (1994), 266:1804.
Altman, "Apparent Virus May Be a Cause of Fetal Cancer in AIDS Patents" New York Times (1994), A1–A2.
Rosenberg et al., "RFLP Subtraction; A Method for Making Libraries of Polymorphic Markers", PNAS (1994), 91:6113–6117.
Hubank et al., "Identifying Differences in mRNA Expression by Representational Difference Analysis of cDNA", Nucleic Acids Research 1994), 22:5640–5648.

(List continued on next page.)

Primary Examiner—Ethan Whisenant
(74) Attorney, Agent, or Firm—Barbara Rae-Ventner; Rae-Venter Law Group, P.C.

(57) ABSTRACT

Nucleic acid sequence probes are provided for the detection of lesions associated with neoplastic cells. The sequences can be used for identifying the locus associated with the lesion, for determining cancer susceptibility of cells, as well as categorizing and characterizing tumor cells for prognosis and therapy.

20 Claims, No Drawings

OTHER PUBLICATIONS

Lux et al., "Analysis of cDNA for Human Erythrocyte Ankyrin Indicates a Repeated Structure with Homology to Tissue–Differentiation and Cell–Cycle Control Proteins", Nature (1990), 344:36–42.

Matsumura et al., "Deletion of Chromosome 17p Loci in Breast Cancer of Cell Detected by Fluorescence in Situ Hybridization", Cancer Research (1992), 52:3474–3477.

Altman (1994) "Apparent Virus May Be a Cause of Fetal Cancer in AIDS Patients" *New York Times,* A1–A2.

Chang et al (1994) *Science 266,* 1865–1869.

Cohen (1994) *Science 266,* 1803–1804.

Hubank et al (1994) *Nucleic Acids Research 22,* 5640–5648.

Kirschbaum, N.E. et al (Dec. 15, 1994) *Blood* 84(12), 4028–4037.

Lasko et al (1991) *Annu. Rev. Genet. 25,* 281–314.

Lisitsyn et al (1993) *Science 259,* 946–951.

Lisitsyn et al (1994) *Nature Genetics 6,* 57–63.

Lisitsyn, N.A. et al (1994) *Cold Spring Harbor Symposia on Quantitative Biology LIX,* 585–587.

Lisitsyn et al (1995) *PNAS USA 92,* 151–155.

Lisitsyn, N. et al (1995) *Methods in Enzymology 254,* 291–304.

Lisitsyn, N.A. et al (Aug. 1995) *TIG 11*(8), 303–307.

Lux et al (1990) *Nature 334,* 36–42.

Matsumura et al (1992) *Cancer Research 52,* 3474–3477.

Pool (1994) *Science 266,* 1804.

Presti, Jr. et al (1991) *Cancer Research 51,* 1544–1552.

Rosenberg et al (1994) *PNAS 91,* 6113–6117.

Schwab et al (1990) *Genes, Chromosomes & Cancer 1,* 181–193.

Solomon et al (1991) *Science 254,* 1153.

* cited by examiner

SEQUENCE LISTING (1) GENERAL INFORMATION:

(iii) NUMBER OF SEQUENCES: 35

(2) INFORMATION FOR SEQ ID NO:1:

(i) SEQUENCE CHARACTERISTICS:
      (A) LENGTH: 324 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "probe"

(xi) SEQUENCE DESCRIPTION: SEQ ID NO:1:

```
AGATCTTCAT TTCTTTAGGG TTCATTGTTG GAGCTTTGTT AGTTTCTTTT AAAGGTATCT      60

TGGCTTCCTG GTTCTTTGTA ATCTGTGTTC TTGTGTTGGT ATCTGCACAT TTTGAGGAGA     120

CAGCTACCTC TTTGACTTTT ATAGGTGTTC TTTGGCAGGG ATAGAACTTC ACTTGTCTAG     180

CCTTTGATTC TGAATAGGCC AACTGGCNGC AGCCTGAGCG GGCAAAGCTT GCTTTGGATT     240

CTGTAGATAG TTGGGCTGCT GCCTTTGCTC TGAGTTTGGG TGGGACTGCT GGCTGGGCTC     300

TGCTATCAGG TGAACCCACA AGCC                                            324
```

(2) INFORMATION FOR SEQ ID NO:2:

(i) SEQUENCE CHARACTERISTICS:

(A) LENGTH: 480 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "probe"

(xi) SEQUENCE DESCRIPTION: SEQ ID NO:2:

| | | | | | |
|---|---|---|---|---|---|
| AGATCTAAAC | GATATCAGCA | TTTATTGATT | CTCTATTTTT | TTTTCTCTAC | TTTAGGTCTT | 60 |
| TTTGGTTCTT | GGTAATATGA | CTGATTTTCT | ATGTAATTCT | GTACATTTTG | GGGCAGGAGA | 120 |
| AAGGGAGGAG | TGGATACTGC | CTTATCACTG | TCAAATGGGG | ATAAAATTCC | CAGTTTCCCA | 180 |
| TGCTGCCTCC | GTTGACACTC | AAGGGGCAC | GGCTCCTCAA | TACTGCTGAG | TGGAAGTGGG | 240 |
| GGTTCCCGTT | TCCCACTAGG | CCTCCATTGT | TAGCTCTGTG | GCTGGAAGGG | GTAGTAATAC | 300 |
| ACTTTTACTG | CTACTGAGCA | TGTGGCCTCT | ACTGACACAA | TGAGGGGCAA | AGGTGGGAAG | 360 |
| GTGCAATACT | TTTACTCTTG | GGCAGGTATG | AAAGTTCTGA | CTCTCCAGAA | GGCCTCTTCT | 420 |
| GATACCACCC | TAGCCAGGAA | AGGGATGGAT | ATTGTTGCCA | TCAGGTGGGA | GTGGAGATCT | 480 |

(2) INFORMATION FOR SEQ ID NO:3:

(i) SEQUENCE CHARACTERISTICS:
(A) LENGTH: 367 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "oligonucleotide"

(xi) SEQUENCE DESCRIPTION: SEQ ID NO:3:

| | | | | | |
|---|---|---|---|---|---|
| AGATCTAAAT | GTCTTCTCTC | CCTCTTTCCC | TCCCTCTCTC | TATGATGTAT | GACTCACTAT | 60 |
| TTTTACGTCT | CACAATGCTT | TATTTTCAAT | TTAATACACT | TCTCTTCATG | TTTCAGTGAC | 120 |
| ACAGTGGAAA | CTGGCCAGAT | GTTAAATAAT | AACATTCTCT | TTTCCTAGTT | ACACAGCAGC | 180 |
| ACTACAGTTT | TTAGCTTTCC | TTGTACTTAA | GTAGGGACCA | TATAACTCAT | CCCCAAAGAA | 240 |
| TGCTGATGGA | ATAATGTGA | GCTTCTTCCA | GGCCTTGCCA | CAAAAACCAT | TCATGAGATT | 300 |
| ATCCACACAT | CTTTCCTCTT | CTACTGCCAT | TTTTAAAAGA | TGTCAGCATC | ATAAGATGGA | 360 |
| AAGATCT | | | | | | 367 |

(2) INFORMATION FOR SEQ ID NO:4:

(i) SEQUENCE CHARACTERISTICS:
(A) LENGTH: 350 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "oligonucleotide"

(xi) SEQUENCE DESCRIPTION: SEQ ID NO:4:

| | | | | | |
|---|---|---|---|---|---|
| AGATCTCTCT | ATCTGGCTGT | CCCAACCAAA | CCCTCCTTTC | CAGCTAAATT | CTTAGGTTGA | 60 |
| CCTTGTGTGC | TCCCAGTCCT | GCAGTCATCC | TGGTTCATTT | TCTTAAACCC | CTCGGTTCTA | 120 |
| AGGGTCTTTC | CAGCCTTTGT | TACCTCAAGT | CATTTCCATG | ATCATCTTAG | ACCTGGTTAA | 180 |
| CACAAGCAGA | CATTTCCAGT | GCTGAATTCT | TAGTGCCATG | ATGGTGGCTT | GTTATCCTTT | 240 |
| CTGCCTCTCA | CCTTCGCACC | TGTTCTCAAA | CCTGCCCAAT | AACCTTGACA | CATCTAAATT | 300 |
| TGACCAGTCT | ACCATCAGAG | TTCCCTGGGG | TACTCGTTAC | AAATAGATCT | | 350 |

(2) INFORMATION FOR SEQ ID NO:5:

(i) SEQUENCE CHARACTERISTICS:
        (A) LENGTH: 322 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:5:

```
AGATCTCCAA ACATTTTGCA ATGCAGAACA CTTAATTTAT GCTTTTTTAG CCCCTCTAAA      60
AGATAAGGTC TTGGTTCCTC GTTCTACTTC CCTACACTTT CCTTCTATCC CCCTGACAGA     120
AACTTACTTA TCTGTCAGAA TTTAACTCCA AGAAGAGTTC TTTCATTTAG CTGACCTACT     180
ACCCAAAACC CTCTATTCAA TTTCTTACTC TCTCCTTCGG AATCATTCCT GATGCCAACA     240
CAGGCTGTCT TTTACTGCTC TGACATACTC GCTTTTCTGT TAATTCAGAT TATTTTCTAA     300
CTTCTTCCAG GGGCTCAGAT CT                                              322
```

(2) INFORMATION FOR SEQ ID NO:6:

(i) SEQUENCE CHARACTERISTICS:
        (A) LENGTH: 419 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:6:

```
AGATCTCAGT GGGAACAGTT CTCTTACAGC CACACGCTTT CTCTCCTCTA ATTCACTGAG      60
AACACCCTCC TTGAGGCCAT CACTGCCAAG AGTAGAGTGA GAATCCTTCC GCTGCATTCA     120
TTTACATTTT AAAGACTAAA TAATGTCATG TCCTCTTCCT CAACTCAACC CTGTAATCAC     180
CTCCCATCAT ACTTTAATAA AATTCAAAAT CACAACCATA ACCTCCAATC CTCGCTTCCT     240
TAGCCCCTCC CTTCCACTTT TTCCTTGCTC TTGAGTTCCA GCCACATTGG TCTCCTTTTG     300
TTCTTCAGGT GCACAAAGCA TGATTCTACT CCAGGGCCAC TGACCTTGTT GTCACCTCTG     360
TCTGGCATAC TCCATTTCCC AAATGCTCCC TGGTTTTCCC CCTTGTTCCT TTTAGATCT      419
```

(2) INFORMATION FOR SEQ ID NO:7:

(i) SEQUENCE CHARACTERISTICS:
        (A) LENGTH: 374 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:7:

```
AGATCTTAAT TGCCAGTAGC CCAGCTGTGT CCTCTCAGCA ACAGAAATCC CACAGCTTCA      60
AGCAGAGTCA GGAAAACCCA GGGATGGTGG TAACAGAAGG TTTTCTGCAG AGGCGCTAGC     120
GAGAACTTAG CATGTACCGC AAGTTTCTTC CAAGAATTAT TGCAATGTGA AAGCATTACA     180
AAAAGGAGGT GTTATCTTCT CATGTGACCT GTGATGTGGA TAGCAGCATC AGAGTTGCCC     240
CACTAGGACA AATGCCCCAA GCCCAGTTCA CCTAGGCCAG CATCATGTTT TCCGACAGTG     300
```

ACTGTAAGCA GAGTTTTAAA GAAGGCATGC CCCTCCAACA TTGCTTGACT CTCCACATAA    360

TGCATTATAG ATCT                                                     374

(2) INFORMATION FOR SEQ ID NO:8:

(i) SEQUENCE CHARACTERISTICS:
        (A) LENGTH: 273 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:8:

AGATCTCTAC TACTGGAATC TTCTAGGAAC TGCCAGTGAG TGCTTGGTTG TCTCTCATCT     60

CACGTCATAC TCAAACCAGC CCTTAAAGAC TAATATTAGT ACCTTCTGCT TACGCGTGTT    120

GAAAACAAGT CTAAGAAGTG ATGTAGCTGT ACAAGATAAG TCCACAAGTC ACAGCGCTGA    180

GTCATGAACC AGGTCTGCCT GCAAAACGTC TGCATTTTCT ATCACACAGG GAAGAGGGTA    240

GTGTCACCAG CTCCTTGGTT AGTACGAAGA TCT                                273

(2) INFORMATION FOR SEQ ID NO:9:

(i) SEQUENCE CHARACTERISTICS:
        (A) LENGTH: 418 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:9:

AGATCTTTTT ATGATGCCTG ACATTATTGT GCTAAGCCTG GGGGAGTTGC TGACACTCTG     60

TCCTCTAGAA CTTTGCAGGA TCCTTGGAGG GTTAAGACCT AAGCCCGCAA GAAAAGTAAC    120

TTCCGAGTGA AGTGTTTGAT TAGATGTCAA ATGAGGAGAC CAGCCAATGA TTTTTATTAC    180

TGATGCCACA GGAAGATAAA GAGAATGCTG TGCCGTGCAA GGTCATTCAG GACAGCTCCT    240

TGGAGACAGG GGCTTCTTAC TGGTTCAGTT CATGGTGGCC CAGGTCTTCC CCTATGACCA    300

CTGAGATGCA ATGACTTTTG GCCAGCTTTC AAAGCCTTAG TAATCTTTCC CAGGCTGCTG    360

GGATTAATAA CTTAGAAGGC CATAGTTCTT GCTTTACTCT TCCTGTGTTC TAAGATCT     418

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:10:

CATTTCTTTA GGGTTCATTG TTGGAGC                                        27

(2) INFORMATION FOR SEQ ID NO:11:

(i) SEQUENCE CHARACTERISTICS:
        (A) LENGTH: 22 base pairs
        (B) TYPE: nucleic acid
        (C) STRANDEDNESS: single (D) TOPOLOGY: linear (ii) MOLECULE TYPE: other nucleic acid
        (A) DESCRIPTION: /desc = "probe"

(xi) SEQUENCE DESCRIPTION: SEQ ID NO:11:

GAGCCCAGCC AGCAGTCCCA CC                                              22

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:12:

CCATGCTGCC TCCGTTGACA CTCA                                            24

(2) INFORMATION FOR SEQ ID NO:13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:13:

TGGCAACAAT ATCCATCCCT TTCCTG                                          26

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:14:

GTCTTCTCTC CCTCTTTCCC TCCC                                            24

(2) INFORMATION FOR SEQ ID NO:15:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:15:

TGGCAGTAGA AGAGGAAAGA TGTGTG                                          26

(2) INFORMATION FOR SEQ ID NO:16:

(i) SEQUENCE CHARACTERISTICS:
        (A) LENGTH: 24 base pairs
        (B) TYPE: nucleic acid (C) STRANDEDNESS: single
            (D) TOPOLOGY: linear (ii) MOLECULE TYPE: other nucleic acid
            (A) DESCRIPTION: /desc = "probe"

(xi) SEQUENCE DESCRIPTION: SEQ ID NO:16:

TGTGCTCCCA GTCCTGCAGT CATC                                                  24

(2) INFORMATION FOR SEQ ID NO:17:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "probe"

(xi) SEQUENCE DESCRIPTION: SEQ ID NO:17:

AGGGAACTCT GATGGTAGAC TGGTC                                                 25

(2) INFORMATION FOR SEQ ID NO:18:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "probe"

(xi) SEQUENCE DESCRIPTION: SEQ ID NO:18:

GCCCCTCTAA AAGATAAGGT CTTGGT                                                26

(2) INFORMATION FOR SEQ ID NO:19:

(i) SEQUENCE CHARACTERISTICS:
            (A) LENGTH: 25 base pairs
            (B) TYPE: nucleic acid
          (C) STRANDEDNESS: single
            (D) TOPOLOGY: linear (ii) MOLECULE TYPE: other nucleic acid
            (A) DESCRIPTION: /desc = "probe"

(xi) SEQUENCE DESCRIPTION: SEQ ID NO:19:

GATCTGAGCC CCTGGAAGAA GTTAG                                                 25

(2) INFORMATION FOR SEQ ID NO:20:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "probe"

(xi) SEQUENCE DESCRIPTION: SEQ ID NO:20:

GGGAACAGTT CTCTTACAGC CACAC                                                 25

(2) INFORMATION FOR SEQ ID NO:21:

(i) SEQUENCE CHARACTERISTICS:
            (A) LENGTH: 25 base pairs (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:21:

ACAGAGGTGA CAACAAGGTC AGTGG                                            25

(2) INFORMATION FOR SEQ ID NO:22:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:22:

CCAGCTGTGT CCTCTCAGCA ACAG                                             24

(2) INFORMATION FOR SEQ ID NO:23:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:23:

ACATGATGCT GGCCTAGGTG AACTG                                            25

(2) INFORMATION FOR SEQ ID NO:24:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:24:

TCTAGGAACT GCCAGTGAGT GCTTG                                            25

(2) INFORMATION FOR SEQ ID NO:25:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:25:

GTACTAACCA AGGAGCTGGT GACAC                                            25

(2) INFORMATION FOR SEQ ID NO:26:

(i) SEQUENCE CHARACTERISTICS:

(A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "probe"

(xi) SEQUENCE DESCRIPTION: SEQ ID NO:26:

GCTAAGCCTG GGGGAGTTGC TGAC                                          24

(2) INFORMATION FOR SEQ ID NO:27:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "probe"

(xi) SEQUENCE DESCRIPTION: SEQ ID NO:27:

GATTACTAAG GCTTTGAAAG CTGGCC                                        26

(2) INFORMATION FOR SEQ ID NO:28:

(i) SEQUENCE CHARACTERISTICS:
            (A) LENGTH: 265 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "probe"

(xi) SEQUENCE DESCRIPTION: SEQ ID NO:28:

GGATCTTATC AAAAAGCAAA GATGCTATCA AAAGGCATTC TCAAGTGTGG ATTCCTTGGA    60

CTAAACTAGA TTATTATTAT TGATGGTTAT GGCCTATTCC ATGAGCTTTT AAAATACTGA   120

TAGCTACTGG CCCCAGCCCC ACCTTCACCC CTATTTATCA AGGTAACCTA ATGGCAGAGC   180

TAGGCATGAA CATAAAGCCA GGCCTGCCTC ACTTCAGAGC CCTTGCTTGT CACCAGATCA   240

GTTTTACCTT GTAATCAATA GATCC                                        265

(2) INFORMATION FOR SEQ ID NO:29:

(i) SEQUENCE CHARACTERISTICS:
            (A) LENGTH: 437 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "probe"

(xi) SEQUENCE DESCRIPTION: SEQ ID NO:29:

GGATCTTTCC TTTCCTCTTC CAGCTTCTGG CAGCCTCAGA TGTTCCCTGG CTTCTGACAA    60

CCCAACTCCA ATCTCTCTGC CTCCATCCCG TCACCACGTG GCCCCTCGCA GGGCTGTATT   120

ATCCCATGTC TGCACTGCTT TCCCTCTGTG AGAGTCTGTC TCTATGTCCA AATGTTGCCC   180

TCTAATAAGG ATACCAGTCA TGTTGAATTA ATTGAATTAG TGTTCACCGT AATGACCTCG   240

TCTTAATTTG AATACATCTG CAAAGACCCT ATTTCCAAAT AAGGACACAT TCACAGTGAT   300

ATAATTTAGA TATTTGTCGC CGCCCAAATC TCATGTTGAA TTTTAATCCC CAATGCTGGA   360

AGTGAGGCCT GGTGGGAGGT ATTTGGATGA TGGCGGATCC CTCATGGCTT GGTGCTATCC   420

TCAAGATAGT AAGATCC                                                          437

(2) INFORMATION FOR SEQ ID NO:30:

(i) SEQUENCE CHARACTERISTICS:
        (A) LENGTH: 335 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:30:

GGATCTGGCT GATAGATGTT GGGGATCCCA TTGCCAGCGC GCTGTCACAT CCCCTCCCCA       60

TTGCCTGTTT CCAGAGCTGA GCCCAGCTTT TCCGTAGCAC TGTGGAGATG AACCTGTCAT      120

GGGGCTCAGA GTGTGGTGTT GGGAGTAGCC TTGGCCTGGT GCCTCTGCCT CACCTGCCCT      180

CCGACTCTGC TGCAAACAGT CAGTTCCTGT TTGTGGGGGC TTGCACAGGG GCAGAGGGAT      240

GGACGAGCTG GCTTGCTCAG AACCTCCTGC CAGCCACAAA CTGANNTGCG CTTGTTTTGG      300

ACGTGGTAGA CTGAGGGGCC CAGGAAGGTA GTCCA                                 335

(2) INFORMATION FOR SEQ ID NO:31:

(i) SEQUENCE CHARACTERISTICS:
        (A) LENGTH: 683 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:31:

GGATCTTTAT TTGCTTCCCA GACTCACCTC TTTCCTGTCG TCCAGGGCAG TTTTAAAGAA       60

ACTGTAGGGA ATTTTATTTC TCTTCTGCCT CTTGAGCCAT TCATTCACGG AGTGCAGGAA      120

GTTCTGGACT AAGGGCCGGC CAGGGAAATA CTGTGGGGAG GAACAAGCGG AANTGGAGAG      180

TGAAAAGCAA TCCCCCAAGT TCCCCGTCCT GCAGATGGTA GGAAGCTATG CAGAAGAAGG      240

CGGGGGGCGG GGGGCNNGGG GCAGTGGGGA GGAGGTTGTG CAAAGTTCCA AAACCACCAG      300

GAAAACATTC TAGCTAAGAC ACAAATATGA CTTCTGTACT ACCTTTGCTC TGGGACACCT      360

GGTAAGGCTA GAAGACAGNG TAGGGAAAGG TGNTTNGCTC TAAATGGGGT GGGGTCCTGG      420

AAGTCTCCCT CTCTCAGACC TCAGGCTCCT GTGCAGCACC CCCCGACCAT GTGCCACCAC      480

TGGGAGGAAG GCTGGAGCAC TTGTGCCCCT TGCCAGAGCT GCTGGGAGCC CTGGGCCACA      540

CAGTCCTGTC TATGGGTGGT CCTCGGATAG AGCTAACTTG CCAACTGACT GGCCAGCTGG      600

GTTAGGTGGG CACGAGACTT TCATTTGGAT TCCATGGGCT GCCAGTGAGG ACCAGCCAGG      660

NCAGGGGCTC ACAGCCAAGA TCC                                              683

(2) INFORMATION FOR SEQ ID NO:32:

(i) SEQUENCE CHARACTERISTICS:
        (A) LENGTH: 662 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:32:

```
GGATCTTCAC ACTGTGCCTC CACTGTCCTC TGAGCCTCAG TTTCCTTACC TGCAACATGA    60
GCAGAAAGTT TGCAGCCACC TCGCCTGGCA GGATGGCCAT GGGGAACCAC AGGAGGGGAG   120
GGGGCAGCGT CGAGGGTCCC ATGGCCAGCC AGCATGGGCC AACCCATGTG TCACAGTTCA   180
TAGAAGGTCT TAGGANCCTG GTCCCTCCCC CTCCCCCTCC CCCCAGGATG TTTGTAGGGT   240
NAGGCAACCG GCAGNNCCTG GTTAAGCCCT GGGGTCTGGA GANCNGTTTC TAACTNCCAG   300
GCCCCTGTGA GCTGCCAAGA CCTCCACCTC CTCCCTAGGG NCCCCGGGGG TCTGTTTGCT   360
CTGTCTGCTT TTGAGAATCA GATTATAATG GGAGCCTGGG TCAGTTTCTG GATTTGTGGC   420
CTCAGGACCT CCCAGAAGGA GCAGAGCTGA AGGCCAAGAG CCTGGCTCCT GTCCTGTCCT   480
GTCACTTACT GCCCTGTGAC CACAGGCAGG TCACTGCACC TCTCTGAGTC ACAGCTTTCT   540
CGTCTTCCAA GCGGGGAGAG TCCTTGAGAC AGGCTGCAAC CATTAGATTC ATTCATTCAA   600
CAAATATTTG CTGAGCATCT ACTATGTGCC AGGCATGTGT GCTGGGACA CAATAGAGAT    660
CC                                                                 662
```

(2) INFORMATION FOR SEQ ID NO:33:

(i) SEQUENCE CHARACTERISTICS:
        (A) LENGTH: 662 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:33:

```
GGATCTCTAT TGTGTCCCCA GCACACATGC CTGGCACATA GTAGATGCTC AGCAAATATT    60
TGTTGAATGA ATGAATCTAA TGGTTGCAGC CTGTTTCAAG GACTCTCCCC GCTTGGAAGA   120
TGAGAAAGCT GTGACTCAGA GAGGTGCAGT GACCTGCCTG TGGTCACAGG GCAGTAAGTG   180
ACAGGACAGG ACAGGAGCCA GGCTCTTGGC CTTCAGCTCT GCTCCTTCTG GGAGGTCCTG   240
AGGCCACAAA TCCAGAAACT GACCCAGGCT CCCATTATAA TCTGATTCTC AAAAGCAGAC   300
AGAGCAAACA GACCCCCGGG NNCCCTAGGG AGGAGGTGGA GGTCTTGGCA GCTCACGGGG   360
GCCTGGAGTT AGAAACNGCT CTTCAGACCC CAGGGCTTAA CCAGGNACCT GCCGGTTGCC   420
TCACCCTACA AACATCCTGG GGGGAGGGGG AGGGGGAGGG ACCAGGNTCC TAAGACCTTC   480
TATGAACTGT GACACATGGG TTGGCCCATG CTGGCTGGCC ATGGGACCCT CGACGCTGCC   540
CCCTCCCCTC CTGTGGTTCC CCATGGCCAT CCTGCCAGGC GAGGTGGCTG CAAACTTTCT   600
GCTCATGTTA CAGGTGAGGA AACTGAGGCT CAGAGGACAG TGGAGGCACA GTGTGAAGAT   660
CC                                                                 662
```

(2) INFORMATION FOR SEQ ID NO:34:

(i) SEQUENCE CHARACTERISTICS:
        (A) LENGTH: 414 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:34:

```
GGATCTGCCT TCGGNCCATG ACTCGCTCAG CAGAAGGCAC TGCCCACAAG TCACCGTTGA    60
```

```
GAAACCCGCC CTGTGAAAAG CAGAAATTGC TCTGGTCACT TCTCCCGGCG CCTGCAGAGA      120

GACCGGCTGT GGCGCTGGTC AGGTAATGGC AGCCATGGCT GGAAACCGGG AACATGGGGC      180

CTGGGCTGGC CTGGTATCTC CTCAGGAAAT GACCGGCCTT CCTGAGGGGC CACCGAACGC      240

GGCCGCTTTG TTTAGTTTCT TTAGGGAAAA AACAAGGCAC AAGTGACATT TGCCTTGGCG      300

TTCTTGACCC TCCCTCTGTC TCGCCTGGGT TTGGGGCCC TTCTCATGGC ACTGTGAGGG       360

GATTCCTCCC TGCCTCCAGC CTCCACCCAC CACCAAAGGG CTGCTCTCCC AGGG            414

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:35:

GATACAGAGG GGCTGTTGAA                                                    20
```

CANCER DETECTION PROBES

This application is a C.I.P of Ser. No. 08/360,096 field Dec. 20, 1994 and now U.S. Pat. No. 5,569,753.

TECHNICAL FIELD

The field of this invention is the identification of lesions in neoplastic cells.

BACKGROUND

The etiology of neoplasia is an extremely complex one. A large number of genes have been found to be associated with normal cells being transformed into tumor cells. Genes that have been identified include genes which enhance cell proliferation and suppress cell proliferation. The present view is that it takes more than one mutation event to take a cell from the phenotype of the normal state to the phenotype of the tumor state.

It appears today that human tumors are genetically heterogeneous by the time of clinical presentation, even though they are rather monoclonal in origin. As the tumor progresses, there may be changes in the genome, such as deletions, insertions, substitutions, chromosomal arm exchanges, gene amplification, and the like. These changes may be associated with various characteristics of the cancer, which are important to the diagnosis and therapy of the patient. Information about the cancer, whether it is aggressive, metastatic, or responsive to a particular treatment as a result of particular genomic changes, can greatly aid in the choice of therapy of the patient. For example, more intensive treatment may be warranted for more aggressive cancers.

There is, therefore, substantial interest in identifying specific genetic differences which are associated with neoplastic cells. These differences provide the opportunity to dentify groups of patients having analogous lesions, where the course of the cancer ay be mapped. In this way, epidemiological data can be adduced as to the nature of he cancer, its response to different therapies, and probable outcomes.

Relevant Literature

U.S. Pat. No. 5,569,753 describes a method called representational difference analysis RDA) for analyzing differences between complex but related genomes.

Salomon et al. (1991) Science 254:1153 and Lasko et al. (1991) Annu. Rev. Genet. 25:281–314 describe genetic lesions found in tumors. Lisitsyn et al. (a)(1993) Science 259:946–951 also describe (RDA). See also Lisitsyn et al.(b) (1993) Nature Genetics, 6:57–63. Presti et al. (1991) Cancer Research 51:1544–1552 report loss of at least portions of the Y chromosome in renal cell carcinoma cells. Schwab and Amler (1990) Genes, Chromosomes and Cancer 1:181–193 report the amplification of N-myc in neuroblastoma cells.

SUMMARY OF THE INVENTION

Nucleic acid probes for detecting cellular lesions associated with tumor cells are provided. The probes are associated with genomic lesions, such as: loss of information, e.g. loss of heterozygosity ("LOH"), hemizygous loss and homozygous loss; gain of information, e.g. gene amplification or acquisition of viral genomes; gene rearrangement; point mutation and the like. By combining the probe with genomic DNA of candidate cells and detecting the lesion, one can evaluate the cancer stage or provide a prognosis. The lesion can be detected by Southern blotting or other hybridization techniques, polymerase chain reaction, and the like.

DESCRIPTION OF THE SPECIFIC EMBODIMENTS

Compositions and methods are provided for detecting genomic lesions associated with cancer. Specific sequences are provided which may be used to detect the lesion in candidate cells, where cells having a normal phenotype may be evaluated for cancer susceptibility or cancer cells may be evaluated as to prognosis and therapy. The sequences may also be used to walk the genome to identify other sequences at the locus of the specific sequence. (See, for example, Molecular Cloning: A Laboratory Manual, 2nd. ed., eds. Sambrook et al., CSHL Press, Cold Spring Harbor, N.Y., 1989, Sections 3.2, 3.9, 3.23, and 9.3) These other sequences at the locus provide additional probes, identify genes associated with the particular lesion and phenotype, and allow for the detection of specific mutations at the locus.

Specific sequences that can be employed in the subject invention are found in the Sequence Listing, infra, as SEQ ID NOS: 1–35. To obtain additional sequences at the locus of the subject sequences, human genomic fragments may be cloned in various sizes, generally ranging from about 10 kbp to 600 kbp or more. By identifying clones to which the probes base pair, one can then walk the probe to identify the sequences 3' and 5' of the probe. See Wahl et al. (1987) P.N.A.S. U.S.A. 84:2160; Triglia (1988) Nucleic Acid Research 16:8186; and Sambrook et al., infra. Depending upon the size of the cloned fragment, one can sequence the entire cloned fragment or further fragment the cloned fragment and sequence a smaller portion. With each extension of the subject sequences, one can then use the additional sequence to identify the next adjacent or contiguous sequence.

The sequences detected by walking the subject sequences and sequences uncovered this way can be screened in an analogous manner to the subject sequences to determine their usefulness as probes. The sequences can be used to screen normal genomes, as well as genomes from tumor cells. Where an unacceptable degree of binding to normal cells is uncovered or after screening a significant number of fresh tumor cells without significant observation of the same lesion, the sequence may be discarded and usually one will not proceed further in walking the DNA. This will be particularly true, where there is a high incidence of the lesion in normal cells. For example, some particular sequences may be found absent in tumors but have a high incidence of being absent in normal human DNA. We call these deletion or insertion polymorphisms. For lesions not associated with gene amplification, generally, the lesion will be absent in 20 randomly selected normal cells, usually absent in 100 randomly selected normal cells, and absent in the normal cells of the source. The lesion is desirably absent in at least a statistically significant proportion of the normal population to provide a cancer diagnostic, but may be present in the normal population, where it is directed to prognosis of an existing tumor, recurrence or remission.

The loci of the subject invention identified by the subject probes will generally be not more than about 300 kbp, usually not more than about 100 kbp and may not exceed about 10 kbp, with the exception that if the lesion comprises an amplified region, the region may be as large as 1 million base pairs in length. The probes employed in this invention as obtained from the specified loci will generally be at least about 18 bp, more usually at least about 30 bp and may be 1kbp or more, usually not exceeding about 40 kbp. While the probes may be either DNA or RNA, as a practical matter the probes will normally entail DNA.

The loci can be present on both autosomal chromosomes or sex chromosomes. For particular types of cancer, there will normally be an association between the type of cancer and the particular lesion. In addition, particular lesions can provide for susceptibility of cells to cancer formation, the aggressiveness of the cancer, particularly as to rate of proliferation and metastatic capability, as well as the response of the cancer cells to particular forms of therapy. The subject loci are associated with carcinomas, as associated with cells from the kidney, colon, esophagus, lung, skin, and brain.

The probes of this invention are further characterized by detecting lesions which are present in neoplastic cells, but not present in normal cells of the same patient, as well as normal cells from other individuals. Frequently, the same lesion may be found in human tumor cell lines and human cells from the same cellular type.

For use in detection of lesions, the probes may be modified by various labels, which will allow for their detection. The labels may be directly detectable, such as fluorescers, enzymes, radioisotopes, particles, and the like. Alternatively, the labels may be indirectly detectable by binding to another molecule which provides for the direct detection. Thus, one may have various ligands which have a complementary pair binding member, where the complementary binding pair member is labeled. Illustrative ligands include biotin, which binds to streptavidin, digoxigenin, which binds to an antibody to digoxigenin, other haptens, and their complementary antibodies, and the like. Other labels may also find application, such as labels providing for chemiluminescence, and channeling, where the probe brings two moieties together, which only interact to provide a signal when in spacial proximity.

The subject probes can be employed in a variety of methodologies to detect the 15 presence of the particular lesion. For example, Southern blotting may be employed with genomic fragments. Alternatively, one may use the polymerase chain reaction, where the subject sequence or portion thereof may be one primer, or distal portions of the subject sequence may be used as two primers. Where the sequence is used as a single primer, a second primer can be employed where the sequence is chosen to have a high likelihood of being present within about 2 kbp of the subject sequence.

Other techniques may involve having a probe with a convenient restriction site, where one end of the probe is tethered to a particle and the other end is labeled with a detectable label, combining the particle bound probes with the sample, followed by separation of the particles and washing away of non-specific DNA. The amount of label in the medium can be detected, followed by addition of the restriction enzyme, separating the particles free of non-bound DNA and detecting the label again. A significant reduction in the amount of label is indicative of the presence of the sequence in the sample. Additionally, one may employ magnetic particles which allow for separation of DNA binding to the subject probe, where the DNA binding to the subject probe may then be detected in a variety of ways, which will be discussed subsequently.

One may also use gel electrophoresis, where it is found that the locus provides for a restriction fragment length polymorphism that is absent in tumor cells but present in normal cells, or the like. Other techniques may include triplex formation and detection using RecA. For further discussion of techniques for detecting specific DNA sequences, see *Molecular Cloning: A Laboratory Manual*, Sambrook et al., eds., Cold Spring Harbor Laboratory, Cold Spring Harbor, N.Y., 1988.

DNA from cells may be obtained by any convenient means, for the most part the techniques are now well established. Cells may be lysed, the DNA precipitated, isolated, redispersed, washed and then fragmented, usually employing restriction enzymes. The particular manner in which the DNA is isolated is not critical to this invention. It is not even necessary to isolate DNA, since fluorescence in-situ-hybridization can be used directly on tissue sections. (See, for example, Matsumura, et al. (1992) Cancer Res. 52:3474–3477.) The significant factor is that one can detect the presence of the lesion in tumor cells, where the presence of the lesion is indicative of susceptibility, prognosis or therapy.

The subject probes can also be used to identify genes which are amplified in tumor cells, where the amplified genes are present in lesions comprising amplified genomic regions. Identification of amplified genes may provide the basis for new therapies, where the amplified copy number of the gene provides for overexpression of the product, which overexpression serves as a target for the therapy. Where the overexpressed product is associated with the abnormally proliferative nature of the tumor cells, agents may be administered which modulate the expression of the gene product. See Pratt, The Anticancer Drugs (1994) pp 306–336. Alternatively, where the product is a cell surface protein, antiproliferative agents which are selective for the surface protein may be administered, where the higher number of surface proteins on the tumor cells due to overexpression will provide for a higher proportion of the antiproliferative agent binding to tumor as opposed to normal cells. Illustrative anticellular proliferative agents that may find use in such methods include antibodies, immunotoxins, and the like.

The probes may be used at various degrees of stringency, depending upon the size of the probe, its composition, the degree of polymorphism anticipated at the homologous site, similarity of the sequence at other sequences, and the like. Relatively mild stringencies may be employed, from about 0.1–1×SSC, 0.1–1% SDS, at temperatures in the range of about 50 to 80° C., or the equivalent thereof.

Kits can be provided where two or more probes are provided from the loci of the subject sequences, which are labeled as previously described. In this manner, the kits can be used for screening human cells as described above.

The following examples are offered by way of illustration and not by way of limitation.

EXPERIMENTAL

Materials and Methods

Cell lines and DNA samples. Renal cell carcinoma cell lines UOK112, UOK114, UOK124, UOK132, UOK108, UOK111, UOK127, UOK146, UOK154 and normal DNAs from the same patients were obtained as described (Angland et al. (1992) *Cancer Research* 52:348–3565). Colorectal cancer cell lines VACO 429, VACO 441, VACO 432, VACO 456, VACO 476, RBX and matched normal DNA were established according to Willson et al. (1987) *J. Cancer Research* 47:2704–2713. Cell line NCI H1770 (small cell lung carcinoma) and EBV-immortalized lymphocytes from the same patient were supplied by J. D. Minna (Southwestern Medical School, Dallas). DNAs from the melanoma tumor cell lines AH-Mel, FF-Mel, BD-Mel and DX-Mel and matched EBV-immortalized cells were the gift of A. Houghton (Memorial Sloan-Kettering Cancer Center, New York). Cell lines A382 (astrocytoma), VM-CUB-2 (bladder cancer), SK-LC-6, SK-LC-13, SK-LC-14, SK-LC-17, SHP-77 (lung cancers), and WILTU-1 (Wilm's tumor) were from the J. Fogh collection (Memorial Sloan-Kettering Cancer Center). All other tumor cell lines were obtained from the ATCC. DNAs NA04844, NA1102 and human/rodent somatic cell hybrid mapping panel #2 were purchased from NIGMS Human Genetic Mutant Cell Repository (Camden, N.J.).

The "standard blotting panel" included Bgl II digests of DNAs from tumor cell lines BD-Mel, AH-Mel (melanomas), T24, VM-CUB-2 (bladder cancers), SK-BR-3, MCF7 (breast cancers), HT-29, SW480, SW620 (colon cancers), A-172, U-118 MG (glioblastomas), A-382 (astrocytoma), NCI H1770, Sk-Lu-1, SK-LC-6, SK-LC-13, SK-LC-14, SK-LC-17, SHP-77 (lung cancers), SK-N-MC, SK-N-SH, IMR-5, (neuroblastomas), G-401 (Wilm's tumor) and normal control DNA NA04844. Allele frequency blots were prepared using Bgl II digests of human DNAs from various races (allele frequency kit, BIOS Laboratories, New Haven). The standard PCR panel included DNAs from tumor cell lines BT-20, MCF7, SK-BR-3, T-47D, BT-549, MDA-MBA-435S, MDA-MB-436, MDA-MB-231, MDA-MD-453, MDA-MB-468 (breast cancers); UOK124, OUK161, UOK114, UOK112, UOK132, UOK154, UOK127, UOK111, UOK146, UOK108 (renal cell carcinomas); LS180, SW403, SW480, HT-29, LoVo, DLD-1, Caco-2, HCT-15, VACO 429, VACO 441 (colon cancers); FF-Mel, BD-Mel, AH-Mel, DX-Mel, HT-144, SK-Mel-2, SK-Mel-3, G-361, WM266-4, Malme-3M (melanomas); T24, VM-CUB-2, UM-UC-3, J82, SCaBER, HT-1376 RT-4, HT-1197 (bladder cancers); and normal control DNA NA04844. Tumor and normal cells were grown as recommended and DNAs were purified using cell culture DNA Maxi kit (Qiagen Inc.). Diploid and aneuploid nuclei were separated by flow cytometry from a biopsy of a patient with Barrett's esophagus (Blount et al. (1991) *Cancer Research* 51:5482–5486) and 100 ng of DNA from each diploid and aneuploid fraction ($10^5$ nuclei each) were purified after lysis in SDS-proteinase K buffer, phenol-chloroform extraction and ethanol precipitation.

Representational difference analysis. The RDA procedure was performed as previously described (See Lisitsyn et al. [1993a and b]) using Bgl II restriction endonuclease (New England Biolabs). When DNAs from flow sorted material were used, 100 ng of each driver and tester was digested with Bgl II and ligated to adapters in a volume of 30 $\mu$l. After ligation, 10 $\mu$g of tRNA (5 mg/ml), 90 $\mu$l of TE buffer, 30 $\mu$l of 10 M ammonium acetate and 380 $\mu$l of ethanol were added. The DNA pellet was recovered by centrifugation and dissolved in 10 $\mu$l of TE buffer. 40 $\mu$l of the DNA ligate was PCR amplified for 20 cycles in a volume of 400 $\mu$l taking two tubes for preparation of driver and two tubes for preparation of tester representation. To get sufficient quantity of DNA, 40 $\mu$l of the product of the first PCR was directly added to each of 12 tubes used for preparation of driver representation and reamplified for 5 cycles in a volume of 400 $\mu$l under standard conditions. The subsequent PCR amplification of tester representation was made in the same way, taking 2 tubes. All subsequent steps were performed as described by Lisitsyn et al.,(a) 1993. RDA difference products were digested with Bgl II, ligated to Bam HI-digested and dephosphorylated pBluescript SK(−) (Strategene), and transformed into *E. coli* XL-Blue competent cells according to the supplier's recommendations.

Characterization and mapping of RDA probes. Plasmid inserts were PCR amplified and those with distinct sizes were selected, purified, and hybridized to Southern blots containing Bgl II representations of driver, tester, one normal male and one normal female DNA prepared as described (Lisitsyn et al., (b) 1993). Sequences present in tester but not in driver representations were hybridized to Southern blots containing Bgl II digested DNAs from the standard blotting panel and to allele frequency blots. These blots were washed two times, 30 min. each, in 0.1×SSC, 0.5% SDS at 68° C. Selected plasmid inserts were sequenced on both strands, using Sequenase T7 DNA polymerase reagent kit (United States Biochemical) as recommended by the supplier. Oligonucleotides derived from the sequences were synthesized, and used for screening the standard PCR panel of DNAs. 250 ng of template was taken per each 100 $\mu$l PCR reaction containing 1 $\mu$M primers.

Amplification was made for 32 cycles. Negative reactions were independently repeated two times.

Mapping of probes on human chromosomes was performed by PCR using 250 ng of DNAs from NIGMS human/rodent somatic cell hybrid mapping panel #2 as templates under the same conditions (Lisitsyn et al., (b) 1993). To sublocalize probes on chromosome 3, DNA from hybrid clone GM 11102 retaining the der(3) t(3; 16) (q13.2;q13) chromosome was used (NIGMS Human Genetic Mutant Cell Repository). Fluorescent in situ hybridization was performed as described (Barker and Schwab (1983) *Gene and Chromosome Analysis*, Vol. 2, 129–154).

Results

Tumor DNA as driver. We performed RDA on sixteen individual pairs of tumor DNAs (used as driver) and matched normal DNAs (used as tester) derived from the same patient, as otherwise cloning of polymorphic differences between different individuals predominates. In all cases, we used Bgl II as the restriction endonuclease to prepare representations. Pure tumor DNAs were isolated from fifteen tumor cell lines (including nine RCC and 6 colon cancer cell lines), and normal DNA was derived from unaffected blood or tissue but not from EBV-immortalized cell lines. In one case we used a fluorescent activated cell sorter to fractionate nuclei from an esophageal cancer biopsy into aneuploid and diploid fractions that were used for preparation of driver and tester DNA, respectively.

In each application of RDA, 2–13 difference products were observed and cloned into plasmids. Plasmid clones were picked at random and inserts of different sizes were analyzed by hybridization to blots containing representations from the normal (tester) and tumor (driver) DNAs, as well as Bgl II representations of normal male and female DNAs. The "informative" probes, that were hybridizing to one band on a blot, and were absent in the driver representation, were taken for further analysis, except for those that derived from the Y chromosome (loss of the Y chromosome information was frequently observed in renal cell carcinomas). In the search for clones detecting single copy sequences which are frequently lost in tumors, informative probes were hybridized to blots containing Bgl II digested DNAs from a standard blotting panel of human tumor cell lines. Those probes that were commonly polymorphic at Bgl II sites were presumed to have arisen by loss of heterozygosity, and were not further studied unless they did not detect any bands in at least one tumor DNA on a blot. Probes of this type, as well as the remaining nonpolymorphic single copy probes, were sequenced, and oligonucleotides derived from the sequence were synthesized to be used for PCR screenin of total genomic DNA from tester, driver, and panels of human tumor cell lines. All probes absent in two or more DNA samples from standard PCR panel were hybridized to allele frequency blots containing Bgl II digests of human DNAs from various races. This way we were able to find two probes which did not hybridize to any sequences in several normal human DNAs. We thus presume that these two probes actually detect hemizygous loss of a deletion polymorphism (see Table 1, footnote c).

Tables 1 and 2 summarize all of our results obtained using tumor DNA as driver.

TABLE 1

|  | Selected for initial characterization | Found to be informative[a] |
|---|---|---|
| A. Renal Cell Carcinoma: | | |
| 1. UOK 112 (male) | 13[b] | 13 (0/13/0) |
| 2. UOK 114 (female) | 12[b] | 4 (3/0/1) |
| 3. UOK 124 (female) | 12[b] | 4 (4/0/0) |
| 4. UOK 132 (male) | 10[b] | 9 (3/6/0) |
| 5. UOK 108 (female) | 2 | 2 (2/0/0) |
| 6. UOK 111 (female) | 5 | 5 (5/0/0) |
| 7. UOK 127 (male) | 3 | 3 (2/1[c]/0) |
| 8. UOK 146 (female) | 3 | 3 (1/1[c]/1) |
| 9. UOK 154 (female) | 5 | 1 (1/0/0) |
| B. Colon Cancer: | | |
| 10. VACO 429 (male) | 2 | 1 (0/0/1) |
| 11. VACO 441 (female) | 3 | 3 (1/0/2) |
| 12. VACO 432 (male) | 2 | 1 (1/0/0) |
| 13. VACO 456 (female) | 2 | 1 (1/0/0) |
| 14. VACO 576 (female) | 2 | 2 (2/0/0) |
| 15. RBX (male) | 2 | 1 (1/0/0) |

TABLE 1-continued

|  | Selected for initial characterization | Found to be informative[a] |
|---|---|---|
| C. Barrett's Esophagus: | | |
| 16. BE 758 (male) (FACS sorted nuclei) | 5 | 5 (0/4/1[d]) |
| Total: | 83 | 58 (27/25/6) |

[a]Entries are a(b, c, d), were a is the total number of probes detecting DNA loss in tumors, judged to be: b—loss-of-heterozygosity, c—hemizygous loss, d—presumably homozygous loss. All but two probes judged to detect hemizygous loss were derived from the Y-chromosome. The difference between quantities of initially selected probes (83) and informative probes (58) was due to the presence of the repeat sequences (9 cases), nonhuman DNA contaminating tester (5 cases) and single copy sequences present in both tester and driver DNAs (11 cases).
[b]The difference products after two rounds of hybridization/selection were cloned; in all the rest of the experiments cloning was performed after three rounds.
[c]Probes 127-1 and 146-1 were found to be deletion polymorphisms, absent on both autosomes of 7 out of 35 and 3 out of 35 of normal humans, respectively.
[d]This result is presumed, but was not confirmed because of the small amount of sorted tumor nuclei available.

9 specific probes were found to detect homozygous loss in tumor cell lines.

These probes were sequenced and are identified as follows: (1) UOK114–18 (SEQ ID NO:01); (2) UOK 146-4 (SEQ ID NO:02); (3) UOK124-6 (SEQ ID NO:03); (4) UOK146-8 (SEQ ID NO:04); (5) UOK132-12 (SEQ ID NO:05); (6) VACO429-6 (SEQ ID NO:06); (7) VACO441-1 (SEQ ID NO:07); (8) VACO441-9 (SEQ ID NO:08); and (9) BE758-6 (SEQ ID NO:09).

TABLE 2

| Probe | Chrom. location | Cell lines with homozygous loss[a,b,c] | Sequences of primers used for PCR | Length of PCR product |
|---|---|---|---|---|
| UOK114-18 (SEQ ID NO:10) (SEQ ID NO:11) | 3p | 1/74 | CATTTCTTTAGGGTTCATTGTTG-GAGC GAGCCCAGCCAGCAGTCCCACC | 293 bp |
| UOK146-4 (SEQ ID NO:12) (SEQ ID NO:13) | 11 | 1/113 | CCATGCTGCCTCCGTTGACACTCA TGGCAACAATATCCATCCCTTTCCTG | 283 bp |
| UOK124-6[d] (SEQ ID NO:14) (SEQ ID NO:15) | 2 | 2/113 | GTCTTCTCTCCCTCTTTCCCTCC TGGCAGTAGAAGAGGAAAGATGTGTG | 319bp |
| UOK146-8[d] (SEQ ID NO:16) (SEQ ID NO:17) | 9 | 13/113 | TGTGCTCCCAGTCCTGCAGTCATC AGGGAACTCTGATGGTAGACTGGTC | 261 bp |
| UOK132-12[d] (SEQ ID NO:18) (SEQ ID NO:19) | 9 | 6/86 | GCCCCTCTAAAAGATAAGGTCTTGGT GATCTGAGCCCCTGGAAGAAGTTAG | 272 bp |
| VACO 429-6 (SEQ ID NO:20) (SEQ ID NO:21) | 20 | 1/86 | GGGAACAGTTCTCTTACAGCCACAC ACAGAGGTGACAACAAGGTCAGTGG | 351 bp |
| VACO 441-1 (SEQ ID NO:22) (SEQ ID NO:23) | 18 | 1/86 | CCAGCTGTGTCCTCTCAGCAACAG ACATGATGCTGGCCTAGGTGAACTG | 268 bp |
| VACO 441-9 (SEQ ID NO:24) (SEQ ID NO:25) | 18 | 1/86 | TCTAGGAACTGCCAGTGAGTGCTTG GTACTAACCAAGGAGCTGGTGACAC | 244 bp |

TABLE 2-continued

| Probe | Chrom. location | Cell lines with homozygous loss[a,b,c] | Sequences of primers used for PCR | Length of PCR product |
|---|---|---|---|---|
| BE758-6 (SEQ ID NO:26) (SEQ ID NO:27) | 3p | 6/86 | GCTAAGCCTGGGGGAGTTGCTGAC GATTACTAAGGCTTTGAAAGCTGGCC | 315 bp | a. The numbers show the ratio of the number of cell lines with apparent homozygous loss to the total number of analyzed cell lines. The primary determination was by PCR.
b. The losses were detected in the following cell lines: probe UOK114-18 in UOK114[c]; probe UOK146-4 in UOK146; probe UOK124-6 in UOK141 and VM-CUB-2; probe UOK146-8 in UOK108, UOK122LN, UOK162, AH-Mel, Malme-3M, UM-UC-3, RT-4, MDA-MB-231, A-382, U-118 MG, A-172, SK-LU-1, and SK-LC-14; probe 132-12 in AH-Mel[c], FF-Mel[c], MDA-MB-231, A-382, U-118 MG, and A-172; probe VACO 429-6 in VACO 429; probes VACO 441-1 and VACO 441-9 in VACO 441, probe BE758-6 in LS180[c], HT-29[c], #
LoVo[c], MDA-MB-436[c,] and VM-CUB-2c. See Materials and Methods for origins of cell lines.
c. PCR data was additionally confirmed by genomic Southern blotting for the indicated cell lines.
d. The probe was found to detect LOH in the initial normal/tumor DNA pair.

Illustrative of the experience with the different probes, RDA was performed using DNA from the renal cell carcinoma cell line UOK146 as driver. One of the probes (UOK146-8) cloned from the third round of hybridization/selection was found to be absent in the Bgl II representation of the tumor DNA. It was further analyzed by Southern blotting and PCR, indicating its frequent homozygous loss in many tumor cell lines. Subsequent PCR analysis of driver and tester DNAs indicated that UOK146-8 in fact detected loss of a small allele of a rare Bgl II polymorphism in the cell line UOK146, and was present in difference product due to loss of heterozygosity rather than homozygous loss in the original tumor. Probe UOK146-8 represents one of three probes detecting apparent homozygous loss in at least one tumor source, but isolated by virtue of loss of heterozygosity in the original tumor (see Table 2).

All probes that detected homozygous loss in at least one tumor cell line were mapped to human chromosomes using a panel of monochromosomal human/rodent somatic cell hybrids (see above). In two cases, an additional human/rodent hybrid was used to resolve location to 3p or 3q (see Table 2).

Tumor DNA as Tester. We also used RDA by taking DNA from tumor cell lines as tester and DNA from matched normals as driver. The cell lines used were melanoma (AH-Mel), small cell carcinoma of the lung (NCIH1770, gift of John Minna), and two RCC cell lines (UOK161 and UOK124). In two cases (AH-Mel and NCIH1770) difference products were observed and were discernible even after the first round of hybridization/selection. In each of these cases individual products cloned from the second round of hybridization/selection detected high-level amplifications (30- to 100-fold) in the tumor DNA used as tester. Additionally, RDA products from NCIH1770 were found to be amplified in a neuroblastoma cell line, IMR-5. The sequences from NCIH1770 were mapped to chromosome 2, and those from AH-Mel were mapped to chromosome 3.

The entirety of the RDA product from the second round of hybridization/selection of the melanoma tumor cell line was used as a probe for FISH to metaphase preparations from the AH-Mel cell line. Two and in some cases three homogeneously staining regions were readily observed in tumor cells with this probe.

Three probes derived from the amplified region of AH-Mel which was mapped to chromosome 3 (3p12) were sequenced and identified as follows: NL81 (265 bp) (SEQ ID NO:28); NL83 (437 bp) (SEQ ID NO:29); and PE23 (335 bp) (SEQ ID NO:30). The presence of amplified sequences from tumors in the RDA product even after one round of hybridization/selection suggested that such difference products would dominate over single copy sequence differences and hence that the detection of gene amplification might not require matched tumor and normal DNAs. To test this idea, we took AH-Mel DNA as tester and either a single or pooled DNA from 10 unrelated humans as driver. In either case, RDA products were observed even after one round of hybridization/selection, and difference products obtained after the second round were found to map to the same amplified region in AH-Mel as the RDA products found using the matched normal DNA as driver.

Additional probes were identified using RDA as described above using tumor DNA as tester, where these probes identify regions of amplification in cell lines derived from breast tumor biopsies. These probes are: (1) WA17 (683 bp) (SEQ ID NO:31) which is derived from an amplified region of chromosome 1 of BBr61 tumor biopsy; (2) WC13 (662 bp) (SEQ ID NO:32) and WC25 (662 bp) (SEQ ID NO:33) which are both derived from an amplified region of chromosome 11 of BBr67 tumor biopsy; and WC41 (414 bp) (SEQ ID NO:34) which is derived from an amplified region of chromosome 17 of BBr67 tumor biopsy. 20 tumor cell lines were screened with the above four probes, the results of which are provided in Table 3, below.

TABLE 3

| Breast Tumor Name | WA17 | WC13 | WC25 | WC41 |
|---|---|---|---|---|
| NsBr5 | − | − | − | − |
| CHTNBr5 | − | − | − | − |
| CHTNBr7 | − | − | − | − |
| CHTNBr8 | − | − | − | − |
| CHTNBr9 | − | − | − | − |
| BBr3 | − | + | + | − |
| BBr8 | − | − | − | − |
| BBr16 | + | − | − | − |

TABLE 3-continued

| Breast Tumor Name | WA17 | WC13 | WC25 | WC41 |
|---|---|---|---|---|
| BBr17 | − | − | − | − |
| BBr31 | − | − | − | + |
| BBr33 | − | − | − | + |
| BBr38 | nd | nd | nd | + |
| BBr44 | − | + | + | − |
| BBr49 | − | − | − | − |
| BBr55 | + | − | − | − |
| BBr60 | − | − | − | − |
| BBr61 | + | − | − | − |
| BBr62 | − | − | − | − |
| BBr66 | − | − | − | − |
| BBr67 | − | + | + | + |
| BBr70 | + | − | − | − |

Based on their extensive overlap in the tumors in which they detect amplifications (See Table 3), it was concluded that two of the probes, WC13 and WC25, are likely derived from the same amplified region. It was also observed that one tumor source, BBr67 has two distinct regions of amplification.

The RDA probe WC41 was observed to fall within the 5' region of the humane gene called PECAM-1, as published in Kirschbaum et al., Blood (1994) 84:4028–4037 at 4030. Based on the published genomic sequence, a probe having the sequence 5'-GATACAGAGGGGCTGTTGAA-3'(SEQ ID NO:35) corresponding to the 3' region of the published sequence was derived and found to detect amplification in the same set of tumors as WC41.

Based on this observation, it was concluded that nearly the whole PECAM-1 gene is amplified in 4 of the 20 breast tumors which were screened for amplification in this study (See Table 3).

When tumor DNA is used as tester, RDA has the potential to detect several types of genetic alterations, including the presence of viral genomes, genomic rearrangements, and a very small proportion of point mutations. Such genetic changes can give rise to restriction endonuclease fragments present in tumor that are not present in the matched normal DNA. RDA also yields probes that detect highly amplified single copy sequences. These probes do not arise because of absolute differences between normal and tumor DNA, but because their relative abundance in tumor has led to their kinetic enrichment during the RDA procedure. For the isolation of highly amplified sequences in tumor DNA, any normal human DNA can be used as driver, providing a means to clone such sequences from any tumor cell.

The subject probes provide means for identifying additional probes at the locus of the subject probes, for detecting susceptibility of cells to neoplasia, and for categorizing tumors in relation to prognosis and therapy. The probes were found by using RDA, which is described in application Ser. Nos. 07/974,447 and 08/149,199, filed Nov. 12, 1992 and Nov. 9, 1993, respectively.

All publications and patent applications mentioned in this specification are herein incorporated by reference to the same extent as if each individual publication or patent application was specifically and individually indicated to be incorporated by reference.

The invention now being fully described, it will be apparent to one of ordinary kill in the art that many changes and modifications can be made thereto without departing from the spirit or scope of the appended claims.

What is claimed is:

1. A method for determining the presence of a lesion associated with neoplasia in human cells, said method comprising:

Combining genomic DNA obtained from said cells with a probe of from 18 bp to 1 kbp that comprises a DNA sequence from a locus of not more than 300 kbp comprising a DNA sequence selected from the group consisting of (SEQ ID NO: 1), (SEQ ID NO: 2), SEQ ID NO: 3), SEQ ID NO: 4), (SEQ ID NO: 5), SEQ ID NO: 6), (SEQ NO: 7), (SEQ ID NO: 8), (SEQ ID NO: 9), (SEQ ID NO: 10), (SEQ ID NO: 11), (SEQ ID NO: 12), (SEQ ID NO: 13), (SEQ ID NO: 14), (SEQ ID NO: 15), (SEQ ID NO: 16), (SEQ ID NO: 17), (SEQ ID NO: 18), (SEQ ID NO: 19), (SEQ ID NO:20), (SEQ ID NO:21), (SEQ ID NO:22), (SEQ ID NO:23), (SEQ ID NO:24), (SEQ ID NO:25), (SEQ ID NO:26), (SEQ ID NO:27) and the fully complementary sequences thereof under hybridization conditions, said probe comprising other than deletion or insertion polymorphisms present in normal cells; and detecting the presence or absence of hybridization of said probe with said genomic DNA as compared to genomic DNA from normal cells as indicative of the presence of said lesion.

2. A method to according to claim 1, wherein said probe is a sequence selected from the group consisting of (SEQ ID NO: 1), (SEQ ID NO: 2), (SEQ ID NO: 3), (SEQ ID NO: 4), (SEQ ID NO: 5), (SEQ ID NO: 6), (SEQ ID NO: 7), (SEQ ID NO: 8), (SEQ ID NO: 9), (SEQ ID NO: 10), (SEQ ID NO: 11), (SEQ ID NO: 12), (SEQ ID NO: 13), (SEQ 11) NO: 14), (SEQ ID NO: 15), (SEQ ID NO: 16), (SEQ ID NO: 17), (SEQ NO: 18), (SEQ ID NO: 19), (SEQ 11) NO: 20), (SEQ ID NO: 21), (SEQ ID NO: 22), (SEQ ID NO: 23), (SEQ ID NO:24), (SEQ 11) NO:25), (SEQ ID NO:26), and (SEQ ID NO:27), and the fully complementary sequences thereof.

3. A method according to claim 1, wherein said probe is labeled to provide a detectable signal.

4. A method according to claim 3, wherein said label is a radioisotope, a hapten, an enzyme, a fluorescer, chemiluminescer, or particle.

5. A method for determining the presence of a lesion associated with neoplasia in human cells, said method comprising:

combining genomic single stranded DNA obtained from said cells with a labeled probe of from 18 bp to 1 kbp that comprises a DNA sequence from a locus of not more than 300 kbp comprising a DNA sequence selected from the group consisting of (SEQ ID NO: 1), (SEQ ID NO: 2), (SEQ ID NO:3), (SEQ ID NO:4), (SEQ ID NO:5), (SEQ ID NO:6), (SEQ ID NO:7), (SEQ ID NO:8), (SEQ ID NO:9), (SEQ ID NO: 10), (SEQ ID NO:11), (SEQ ID NO:12), (SEQ ID NO:13), (SEQ ID NO:14), (SEQ ID NO:15), (SEQ ID NO:16), (SEQ ID NO:17), (SEQ ID NO:18), (SEQ ID NO:19), (SEQ ID NO:20), (SEQ ID NO:21), (SEQ ID NO:22), (SEQ ID NO:23), (SEQ ID NO:24), (SEQ ID NO:25), (SEQ ID NO:26), (SEQ ID NO:27) and the fully complementary sequences thereof under hybridization conditions, said probe comprising other than deletion or insertion polymorphisms present in normal cells; and detecting the presence or absence of hybridization of said probe with said genomic DNA as compared to genomic DNA from normal cells as indicative of the presence of said lesion.

6. A method according to claim 5, wherein said probe is labeled to provide a detectable signal.

7. A method according to claim 6, wherein said label is a radioisotope, a hapten, an enzyme, a fluorescer, chemiluminescer, or particle.

8. A DNA of from 18 bp to 1 kbp comprising a sequence selected from the group consisting of (SEQ ID NO: 1), (SEQ ID NO:2), (SEQ ID NO:3), (SEQ ID NO:4), (SEQ ID NO:5), (SEQ ID NO:6), (SEQ ID NO:7), (SEQ ID NO:8), (SEQ ID NO:9), (SEQ ID NO:10), (SEQ ID NO:11), (SEQ ID NO:12), (SEQ ID NO:13), (SEQ ID NO:14), (SEQ ID NO:15), (SEQ ID NO:16), (SEQ ID NO:17), (SEQ ID NO:18), (SEQ ID NO:19), (SEQ ID NO:20), (SEQ ID NO:21), (SEQ ID NO:22), (SEQ ID NO:23), (SEQ ID NO:24), (SEQ ID NO:25), (SEQ ID NO:26), (SEQ ID NO:27), (SEQ ID NO:28), (SEQ ID NO:29), (SEQ ID NO:30), (SEQ ID NO:31), (SEQ ID NO:32), (SEQ ID NO:33), (SEQ ID NO:34), (SEQ ID NO: 35) and the fully complementary sequences, thereof or a labeled DNA sequence selected from the group consisting of (SEQ ID NO: 1), (SEQ ID NO:2), (SEQ ID NO:3), (SEQ ID NO:4), (SEQ ID NO:5), (SEQ ID NO:6), (SEQ ID NO:7) (SEQ ID NO:8), (SEQ ID NO:9), (SEQ ID NO: 10), (SEQ ID NO: 11), (SEQ ID NO:12), (SEQ ID NO:13), (SEQ ID NO:14), (SEQ ID NO:15), (SEQ ID NO:16), (SEQ ID NO:17), (SEQ ID NO:18), (SEQ ID NO:19), (SEQ ID NO:20), (SEQ ID NO:21), (SEQ ID NO:22), (SEQ ID NO:23), (SEQ ID NO:24), (SEQ ID NO:25), (SEQ ID NO:26), (SEQ ID NO:27) (SEQ ID NO:28), (SEQ ID NO:29), (SEQ ID NO:30), (SEQ ID NO:31) (SEQ ID NO:32) (SEQ ID NO:33), (SEQ ID NO:34), (SEQ ID NO: 35) and the fully complementary sequences thereof, wherein said label is capable of being detected.

9. A DNA probe according to claim 8, wherein said label is a radioisotope, a hapten, an enzyme, a fluorescer, a chemiluminescer, or a particle.

10. A DNA probe useful for detecting lesions associated with neoplasia in human cells, said probe of from 18 bp to 1000 bp comprising a sequence selected from the group consisting of (SEQ ID NO: 1), (SEQ ID NO: 2), (SEQ ID NO: 3), (SEQ ID NO: 4), (SEQ ID NO: 5), (SEQ ID NO: 6), (SEQ 11) NO: 7), (SEQ ID NO: 8), (SEQ ID NO: 9), (SEQ ID NO: 10), (SEQ ID NO: 11), (SEQ ID NO: 12), (SEQ ID NO: 13), (SEQ ID NO: 14), (SEQ ID NO: 15), (SEQ ID NO: 16), (SEQ ID NO: 17), (SEQ ID NO: 18), (SEQ ID NO: 19), (SEQ ID NO: 20), (SEQ ID NO:21), (SEQ ID NO:22), (SEQ ID NO:23), (SEQ ID NO:24), (SEQ ID NO:25), (SEQ ID NO:26), (SEQ ID NO:27), (SEQ ID NO:28), (SEQ ID NO:29), (SEQ ID NO:30), (SEQ ID NO:31), (SEQ ID NO:32), (SEQ ID NO:33), (SEQ ID NO:34) and (SEQ ID NO:35).

11. A kit comprising at least two DNAs according to claim 8.

12. A method for identifying a DNA probe useful for detecting lesions associated with neoplasia in human cells, said method comprising the steps of:

(a) walking genomic DNA with a DNA sequence selected from the group consisting of (SEQ ID NO:1), (SEQ ID NO:2), (SEQ ID NO:3), (SEQ ID NO:4), (SEQ ID NO:5), (SEQ ID NO:6), (SEQ ID NO:7), (SEQ ID NO:8), (SEQ ID NO:9), (SEQ ID NO:10), (SEQ ID NO:11), (SEQ ID NO:12), (SEQ ID NO:13), (SEQ ID NO:14), (SEQ ID NO:15), (SEQ ID NO:16), (SEQ ID NO:17), (SEQ ID NO:18), (SEQ ID NO:19), (SEQ ID NO:20), (SEQ ID NO:21), (SEQ ID NO:22), (SEQ ID NO:23), (SEQ ID NO:24), (SEQ ID NO:25), (SEQ ID NO:26), (SEQ ID NO:27), (SEQ ID NO:28), (SEQ ID NO:29), (SEQ ID NO:30), (SEQ ID NO:31), (SEQ ID NO:32), (SEQ ID NO:33), (SEQ ID NO:34), (SEQ ID NO:35) and the fully complementary sequences thereof, to obtain an extended sequence as a secondary probe; and (b) screening said secondary probe with at least one of normal cells and tumor cells to determine whether said secondary probe is informative of a lesion associated with neoplasia in human cells.

13. The method according to claim 12, further comprising the step of walking genomic DNA with said secondary probe to obtain at least one successive probe and screening said at least one successive probe with at least one of normal cells and tumor cells to determine whether said at least one successive probe is informative of a lesion associated with neoplasia in human cells.

14. A method for determining the presence of a lesion associated with neoplasia in human cells, said method comprising:

Combining genomic DNA obtained from said cells with a probe of from 18 bp to 1 kbp that comprises a DNA sequence from a locus of not more than 300 kbp comprising a DNA sequence selected from the group consisting of (SEQ ID NO: 28), (SEQ ID NO: 29), (SEQ ID NO: 30), (SEQ ID NO: 31), (SEQ ID NO: 32), (SEQ ID NO: 33), (SEQ ID NO: 34), (SEQ ID NO: 35) and the fully complementary sequences thereof under hybridization conditions, said probe comprising other than deletion or insertion polymorphisms present in normal cells; and detecting the presence of hybridization of said probe with said genomic DNA as indicative of the presence of said lesion.

15. A method according to claim 14, wherein said probe is a sequence selected from the group consisting of (SEQ ID NO: 28), (SEQ ID NO: 29), (SEQ ID NO: 30), (SEQ ID NO: 31), (SEQ ID NO: 32), (SEQ ID NO: 33), (SEQ ID NO: 34), (SEQ ID NO: 35) and the fully complementary sequences thereof.

16. A method according to claim 14, wherein said probe is labeled to provide a detectable signal.

17. A method according to claim 16, wherein said label is a radioisotope, a hapten, an enzyme, a fluorescer, a chemiluminescer, or a particle.

18. A method for determining the presence of a lesion associated with neoplasia in human cells, said method comprising: combining genomic single stranded DNA obtained from said cells with a labeled probe of from 18 bp to 1kbp that comprises a DNA sequence from a locus of not more than 300 kbp comprising a DNA sequence selected from the group consisting of (SEQ ID NO: 28), (SEQ ID NO: 29), (SEQ ID NO: 30), (SEQ ID NO: 31), (SEQ ID NO: 32), (SEQ ID NO: 33), (SEQ ID NO: 34), (SEQ ID NO: 35) and the fully complementary sequences thereof under the hybridization conditions, said probe comprising other than deletion or insertion polymorphisms present in normal cells and;

detecting the presence of hybridization of said probe with said genomic DNA as indicative of the presence of said lesion.

19. A method according to claim 18, wherein said probe is labeled to provide a detectable signal.

20. A method according to claim 19, wherein said label is a radioisotope, a hapten, an enzyme, a fluorescer, a chemiluminescer, or a particle.

* * * * *

UNITED STATES PATENT AND TRADEMARK OFFICE
CERTIFICATE OF CORRECTION

PATENT NO.   : 6,350,576 B1
DATED        : February 26, 2002
INVENTOR(S)  : Michael Wigler et al.

It is certified that error appears in the above-identified patent and that said Letters Patent is hereby corrected as shown below:

<u>Title page,</u>
Item [75], "Michael Wigler's" address "Lloyd, NY" should be -- Cold Spring Harbor, NY --.

<u>Column 1,</u>
Line 3, "field" should read -- filed --.
Line 37, "dentify" should read -- identify --.
Line 43, "RDA)" should read -- (RDA) --.

<u>Column 3,</u>
Line 36, before "presence", delete "15".

<u>Column 12,</u>
Line 14, following "tumor", insert -- DNA --.
Line 31, "kill" should read -- skill --.

Signed and Sealed this

Twenty-ninth Day of July, 2003

JAMES E. ROGAN
*Director of the United States Patent and Trademark Office*